United States Patent
Sekhon (10) Patent No.: US 12,042,397 B2
(45) Date of Patent: Jul. 23, 2024

(54) INTERVERTEBRAL IMPLANT

(71) Applicant: SpinePoint, LLC, Reno, NV (US)

(72) Inventor: Lali Sekhon, Reno, NV (US)

(73) Assignee: Spinepoint, LLC, Reno, NV (US)

( * ) Notice: Subject to any disclaimer, the term of this patent is extended or adjusted under 35 U.S.C. 154(b) by 0 days.

(21) Appl. No.: 18/529,340

(22) Filed: Dec. 5, 2023

(65) Prior Publication Data
US 2024/0115395 A1   Apr. 11, 2024

Related U.S. Application Data

(63) Continuation of application No. PCT/US2023/062569, filed on Feb. 14, 2023.

(60) Provisional application No. 63/268,034, filed on Feb. 15, 2022.

(51) Int. Cl.
*A61F 2/44* (2006.01)
*A61F 2/30* (2006.01)

(52) U.S. Cl.
CPC ........ *A61F 2/4425* (2013.01); *A61F 2/30907* (2013.01); *A61F 2002/30112* (2013.01); *A61F 2002/30156* (2013.01); *A61F 2002/30158* (2013.01); *A61F 2002/30179* (2013.01); *A61F 2002/30326* (2013.01); *A61F 2002/30909* (2013.01); *A61F 2002/3092* (2013.01); *A61F 2002/443* (2013.01)

(58) Field of Classification Search
CPC ................ A61F 2/4425; A61F 2/30907; A61F 2002/30112; A61F 2002/30156; A61F 2002/30158; A61F 2002/30179; A61F 2002/30326; A61F 2002/30909; A61F 2002/3092; A61F 2002/443

USPC ...... 623/17.11, 17.13, 17.15, 17.16; 606/246
See application file for complete search history.

(56) References Cited

U.S. PATENT DOCUMENTS

| | | |
|---|---|---|
| 5,989,291 A | 11/1999 | Ralph et al. |
| 6,179,874 B1 | 1/2001 | Cauthen |
| 6,743,257 B2 | 6/2004 | Castro |
| 7,867,276 B2 | 1/2011 | Matge et al. |
| D676,966 S * | 2/2013 | Hurlbert ............... D24/155 |
| 8,603,176 B2 | 12/2013 | Duplessis et al. |

(Continued)

OTHER PUBLICATIONS

International Search Report, Patent Cooperation Treaty, Jun. 27, 2023.

(Continued)

*Primary Examiner* — Eduardo C Robert
*Assistant Examiner* — David C Comstock
(74) *Attorney, Agent, or Firm* — Simpson & Simpson, PLLC (57) ABSTRACT

An intervertebral implant for positioning within an intervertebral space between adjacent first and second vertebral bodies. The intervertebral implant includes an implant body extending along a longitudinal axis of the intervertebral implant that is adapted to align with a vertical axis of the spine. The implant body includes a top plate and a bottom plate disposed longitudinally opposite and spaced apart from the top plate along the longitudinal axis. Further, the implant body includes at least one cross-arm obliquely extending between the top plate and the bottom plate. Furthermore, the implant body includes a lattice structure disposed at least between the at least one cross-arm and the top plate and between the at least one cross-arm and the bottom plate.

20 Claims, 7 Drawing Sheets

(56) References Cited

U.S. PATENT DOCUMENTS

| | | |
|---|---|---|
| 11,039,933 B2 | 6/2021 | Gregersen et al. |
| 2008/0154379 A1* | 6/2008 | Steiner .................. A61F 2/4455 623/17.16 |
| 2010/0004688 A1* | 1/2010 | Maas ................. A61B 17/7065 606/248 |
| 2011/0093075 A1* | 4/2011 | Duplessis ............. A61F 2/4425 623/17.16 |
| 2014/0316524 A1* | 10/2014 | Zimmers ............. A61F 2/30771 623/17.16 |
| 2019/0000636 A1* | 1/2019 | Kim ......................... A61F 2/447 |
| 2019/0274841 A1 | 9/2019 | Hawkes et al. |
| 2019/0336305 A1* | 11/2019 | Joly ................... A61F 2/30734 |
| 2020/0188128 A1 | 6/2020 | Sack |
| 2020/0289288 A1* | 9/2020 | Müller ................... B33Y 80/00 |
| 2020/0345506 A1 | 11/2020 | Ryan et al. |
| 2021/0330473 A1* | 10/2021 | Hunt ..................... A61F 2/2846 |
| 2023/0165690 A1* | 6/2023 | Blain .................. A61F 2/30771 623/17.11 |
| 2023/0404773 A1* | 12/2023 | Gantick ............. A61F 2/30771 |

OTHER PUBLICATIONS

Written Opinion of the International Searching Authority, Patent Cooperation Treaty, Jun. 27, 2023.

* cited by examiner

INTERVERTEBRAL IMPLANT

CROSS-REFERENCE TO RELATED APPLICATIONS

This application is the U.S. national stage application filed pursuant to 35 U.S.C. 365(c) and 120 as a continuation of International Patent Application No. PCT/US2023/062569, filed on Feb. 14, 2023, which application claims priority to U.S. Patent Application No. 63/268,034 filed on Feb. 15, 2022, which applications are incorporated herein by reference in their entireties.

TECHNICAL FIELD

The present disclosure generally relates to spinal implants and, more particularly, to artificial intervertebral implants for providing intervertebral distraction and dynamic spinal stabilization.

BACKGROUND

The spine is a complicated structure made up of various anatomical components, which, while being flexible, provides structure and stability for the body. The spine is made up of vertebrae, each having a vertebral body of a generally cylindrical shape. Opposed surfaces of adjacent vertebral bodies are connected together and separated by intervertebral discs, comprised of a fibrocartilaginous material. The vertebral bodies are also connected to each other by a complex arrangement of ligaments acting together to limit excessive movement and to provide stability. A stable spine is important for preventing incapacitating pain, progressive deformity, and neurological compromise.

The anatomy of the spine allows motion (translation and rotation in a positive and negative direction) to take place without much resistance but as the range of motion reaches physiological limits, the resistance to motion gradually increases, thereby bringing such motion to a gradual and controlled stop.

Intervertebral discs (hereinafter referred to as the "discs") are highly functional and complex structures. They contain a hydrophilic protein substance that is able to attract water thereby increasing its volume. The protein, also called the nucleus pulposis, is surrounded and contained by a ligamentous structure called the annulus fibrosis (or "annulus"). The discs perform a load or weight bearing function, wherein they transmit loads from one vertebral body to the next while providing a cushion between adjacent bodies. The discs also allow movement to occur between adjacent vertebral bodies but within a limited range. In this way, the mobility (i.e., range of motion) of the spine is dependent upon the stiffness of the discs in a given segment (e.g., a pair of adjacent vertebrae) of the spine. As will be understood, such stiffness would vary depending upon the location of the spinal segment along the length of the spine. For example, a segment located in the cervical region of the spine may have a lower stiffness (i.e., greater range of motion) as compared to a segment located in the thoracic region. It will also be understood that the relative degrees of stiffness of segments would vary from one individual to another depending upon various factors that may affect the physical limits of each segment.

As will be understood, a certain amount of stiffness in spinal segments is needed for normal or symptom-free functioning. The amount of stiffness in a spinal segment can be defined as the ratio of an applied load to the induced displacement with translation or rotation. A loss of stiffness results in exaggerated movement of the associated spinal segment such as, for example, when torque is applied. From a biomechanical perspective, loss of stiffness indicates spinal instability. Exaggerated motion caused by instability or loss of physiological stiffness may result in greater stress in adjacent innervated connective tissue and may also lead to a greater risk of nerve-root compression and irritation in the foramina.

A normally functioning intervertebral disc has the capacity to store, absorb and transmit energy applied to it. The fluid nature of the nucleus enables it to translate vertically applied pressure (axial loading) into circumferential tension in the annulus. Due to a number of factors such as age, injury, disease, etc., intervertebral discs may lose their dimensional stability and collapse, shrink, become displaced, or otherwise damaged. It is common for diseased or damaged discs to be replaced with prosthetics, or implants. One of the known methods involves replacement of a damaged disc with a spacer, which is implanted into the space originally occupied by the disc (the disc space).

Motion segment stiffness depends on the presence of a distracting force, or a force that attempts to produce positive Y-axis translation. This constant distracting force keeps not only the annular ligaments surrounding the disc space taut but also other ligaments located anteriorly and posteriorly in the spine. The motion segment then functions in a stiffer and more stable manner whereby excessive motion causing instability, pain, and neurological symptoms are reduced or eliminated. The cushioning and balancing of loads applied to the disc space are also important in attempting to restore and preserve normal functionality of the spine. Forces normally applied to the disc primarily occur from vertical loading (compression) or, in biomechanical terms, negative Y-axis translation. A device that has the ability to resist or cushion negative Y-axis translation will be able to preserve disc height. However, a device that has the ability to generate positive Y-axis translation (distraction) would not only be able to resist axial or Y-axis compression but would also be able to dynamically balance these loading forces acting on the disc space. Therefore, such a device would not only provide cushioning but also elastic support and balance, thereby restoring normal physiological disc function and mechanics.

Further, other than the above-mentioned issues, the intervertebral implants are also required to meet various regulations and standards for mechanical strength provided by one or more health regulatory bodies, for example, the United States Food and Drug Administration (FDA). Such regulations mandate that the intervertebral implants possess one or more properties for optimal functioning when positioned in the spine. One such property is the mechanical stiffness (i.e., the ratio of the applied load to the induced displacement) of the intervertebral implant, which must be evaluated under static and dynamic axial compression, compression-shear, and torsional loads. Accordingly, the intervertebral implants must have a stiffness within predefined limits, as set by the regulatory body, to be able to withstand the physiologic loading in the spine while avoiding significant subsidence into the adjacent vertebral bodies or mechanical failure of the implant. Additionally, intervertebral implants that are too stiff may contribute to the risk for adjacent segment disease (ASD) causing degenerative changes above and below the fusion segment. Therefore, generally, the implant may be intended to possess minimum permissible stiffness to avoid excessive stiffness in the corresponding segment and simulate the natural stiffness of the normal discs as much as possible.

Disc replacement implants that allow some movement between adjacent vertebrae have been proposed. An example of such an implant is taught in U.S. Pat. No. 6,179,874 (hereinafter '874 patent). The implant of the '874 patent is formed from two hemicylindrical elements, each engaging one of an adjacent pair of vertebrae. An articulating ball-and-socket joint between the two elements resists compression and lateral movement between the vertebra but allows pivotal movement. U.S. Pat. No. 5,989,291 describes an intervertebral spacer device having a pair of opposing plates for seating against opposing vertebral bone surfaces, separated by at least one spring mechanism. Further, U.S. Pat. No. 6,743,257 describes a generally "U" shaped spacer having a plurality of upper and lower arms protruding joined together at a fulcrum point forming the base of the "U". U.S. Pat. No. 7,867,276 also describes a "U" shaped structure for an implant including two side walls resting against the vertebral endplates and an intermediate wall joining the supporting walls. Furthermore, U.S. Pat. No. 11,039,933 describes an interbody spinal fusion implant that includes spaced apart top and bottom plates so that a cavity is formed therebetween and a sidewall including a plurality of outer struts and inner struts extending between the top wall and the bottom wall. A further implant is described in Applicant's U.S. Pat. No. 8,603,176.

However, there still exists a need for an intervertebral implant that not only overcomes the deficiencies of prior art solutions but also meets the regulated standards of stiffness, such as those provided by the FDA. More particularly, there exists a need for an intervertebral implant that is able to balance the reconstruction of spinal structures by restoring motion segment stiffness while at the same time allowing for the preservation of motion, such as translation motion along the Y (or vertical) axis.

SUMMARY OF THE DESCRIPTION

In an aspect, an intervertebral implant is provided. The implant includes an implant body that extends along a longitudinal axis of the implant. The implant body includes a top plate and a bottom plate disposed longitudinally opposite and spaced apart from the top plate along the longitudinal axis. At least one cross-arm obliquely extends between the top plate and the bottom plate. The implant body further includes a lattice structure disposed at least between the at least one cross-arm and the top plate and between the at least one cross-arm and the bottom plate.

In another aspect, an intervertebral implant is provided. The implant includes an implant body that extends along a longitudinal axis of the implant and defines and surrounds a central cavity. The implant body includes a top plate and a bottom plate disposed longitudinally opposite and spaced apart from the top plate along the longitudinal axis. The implant body further includes a first cross-arm and a second cross-arm. The first cross-arm obliquely extends between the top plate and the bottom plate on the first side of the implant body. Similarly, the second cross-arm obliquely extends between the top plate and the bottom plate on the second side of the implant body.

BRIEF DESCRIPTION OF THE DRAWINGS

Embodiments will now be described with reference to the appended drawings wherein.

DETAILED DESCRIPTION

At the outset, it will be appreciated that like drawing numbers on different drawing views identify identical, or functionally similar, structural elements of the invention. It will also be appreciated that figure proportions and angles are not always to scale in order to clearly portray the attributes of the present invention.

In the following description, the terms "superior", "top", "inferior", "bottom", "anterior", "posterior", and "lateral" will be used. These terms are meant to describe the orientation of the implants of the present disclosure when positioned in the spine and are not intended to limit the scope of the subject matter in any way. For instance, "superior" or "top" refers to a top portion of the implant and "posterior" refers to that portion of the implant (or other spinal components) facing the rear of the patient's body when the spine is in the upright position. Similarly, the term "inferior" or "bottom" will be used to refer to the bottom portions of the implant while "anterior" will be used to refer to those portions that face the front of the patient's body when the spine is in the upright position. With respect to views shown in the accompanying figures, the term "coronal" will be understood to indicate a longitudinal plane extending between lateral ends thereby separating the body into anterior and posterior portions. Similarly, the term "lateral" will be understood to mean a position parallel to a coronal plane. The term "sagittal" will be understood to indicate a plane extending anteroposterior thereby separating the body into lateral portions. The term "axial" will be understood to indicate a plane separating the body into superior and inferior portions. It will be appreciated that these positional and orientation terms are not intended to limit the disclosure to any particular orientation but are used to facilitate the following description.

In addition, the term "vertical" is used herein to refer to the "Y", or longitudinal axis of the spine. It will be understood that the longitudinal axis may be referred to generally as "vertical" in the context where the individual is upright. It will also be appreciated that the spine is normally not linear and that a number of curved regions exist. As such, the term "vertical" will be understood to mean a relative orientation of structures in a spinal segment and is not intended to mean orientation with respect to an external reference point.

The present disclosure provides artificial intervertebral implants for replacing intervertebral discs and be positioned between two adjacent vertebral bodies to restore segmental stiffness, preserve motion between the vertebral bodies and simulate other spinal functions, such as those performed by the natural intervertebral discs. It will be appreciated that the implant(s) of the present disclosure can be designed for various types of surgeries and may be used at different locations on the spine and potentially other places such as, foot and ankle. Further, the implant of the present disclosure can also be used with artificial vertebral bodies. Examples of the implants may include, but not limited to, an anterior lumbar interbody fusion (ALIF) implant, a posterior lumbar interbody fusion (PLIF) implant, a transforaminal lumbar interbody fusion (TLIF) implant, a lateral lumbar interbody fusion (LLIF) implant, an anterior cervical decompression and fusion (ACDF) implant, and so on.

Figure 1:
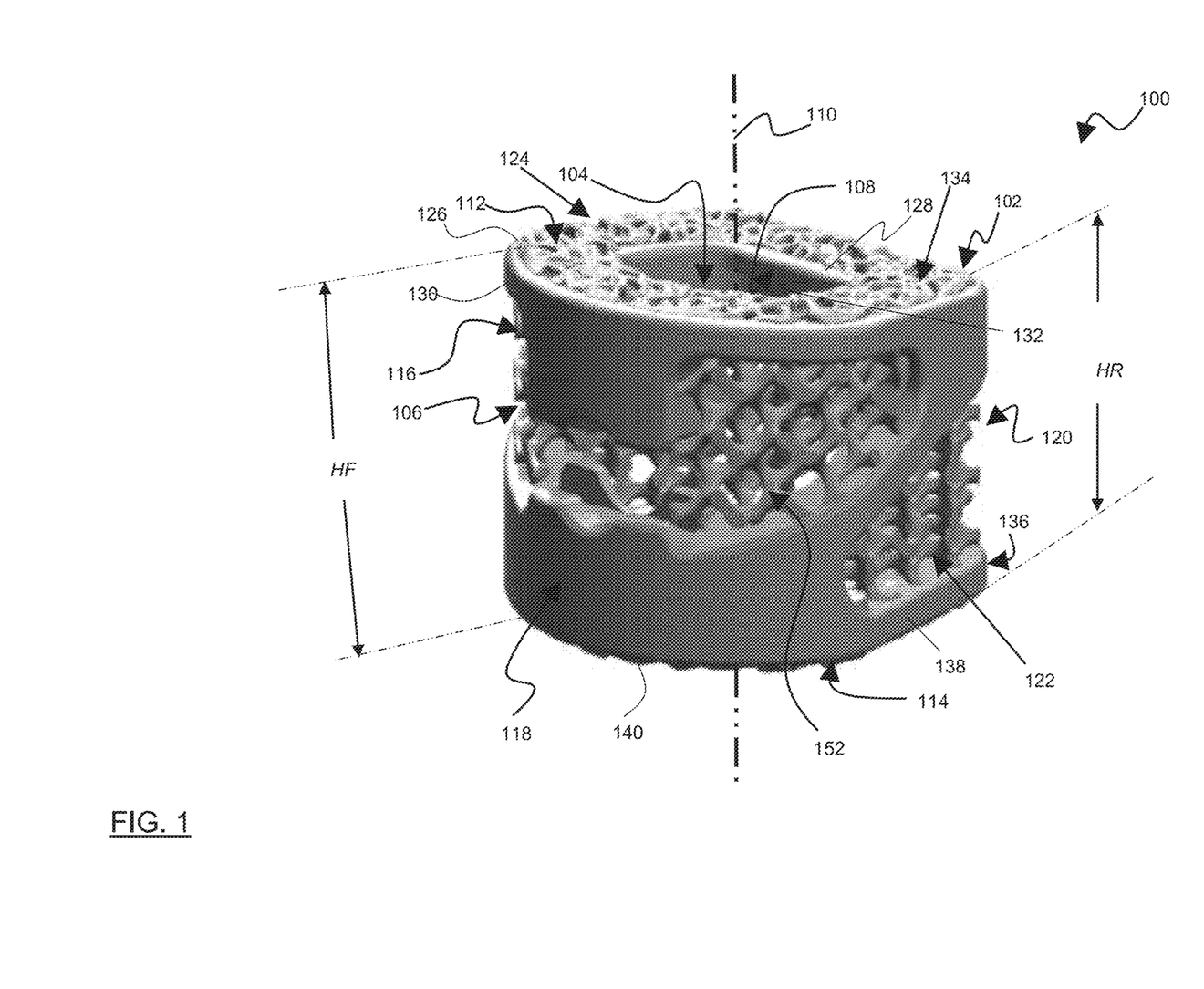
FIG. 1 illustrates an intervertebral implant, in accordance with an aspect of the present disclosure.

FIG. 1 illustrates an example of an intervertebral implant 100 in accordance with an embodiment of the present disclosure. The intervertebral implant 100, hereinafter referred to as the implant 100, has an implant body 102 that serves as an annulus defining and surrounding a hollow central cavity 104. The implant 100 further defines an external surface 106 and a radially opposing internal surface 108 facing and communicating with the central cavity 104. The hollow central cavity 104 may be configured to receive a bone graft material therein, for example, during use of the implant 100. For example, bone allograft or autograft may be received in the central cavity 104, however, in some other examples, bone graft substitutes, such as cadaveric bone (allografts), synthetic bone graft extenders (including but not limited to various combinations of hydroxyapatite and calcium sulfate), bone morphogenetic proteins (BMP), or the like may also be used instead.

The implant body 102 vertically extends along a longitudinal axis 110 of the implant 100 which is configured to align with a Y-axis of the spine when the implant 100 is in use. The implant body 102 includes a top plate 112 and a bottom plate 114 positioned longitudinally opposite and spaced apart from the top plate 112 along the longitudinal axis 110. For example, when the implant 100 is positioned between two adjacent vertebral bodies, the top plate 112 may be positioned to face the superior portion of the spine and engage with a vertebral body positioned above the implant 100, whereas the bottom plate 114 may be positioned to face the inferior portion of the spine and engage with a vertebral body positioned below the implant 100, such as when the spine is in an upright position.

The implant body 102 further includes an encircling wall 116 extending between the top plate 112 and the bottom plate 114 and surrounding the central cavity 104. The top plate 112, the bottom plate 114 and the encircling wall 116 define a front portion 118, a rear portion 120, a first side 122 and a second side 124 of the implant body 102 and/or the implant 100. For example, the front portion 118 may correspond to an anterior portion of the implant 100 that may be configured to face the front of the patient's body whereas the rear portion 120 may correspond to a posterior portion of the implant 100 that may be configured to face the rear of the patient's body when the implant 100 is positioned in the spine. Similarly, the first and the second sides 122, 124 may correspond to the opposing lateral sides of the implant 100. It may be appreciated that these positions and orientation terms are solely to facilitate understanding of the present disclosure and are not intended to limit the disclosure to any particular orientation.

Further, the implant 100 may have a rear height HR and a front height HF of the implant 100. In some implementations, the rear height HR may be less than or equal to the front height HF. For example, the height differences between portions (e.g., HR and HF) of the implant 100 may be intended to maintain or mimic the relative angular positioning of vertebrae adjacent to where the implant is inserted. It may be appreciated that the height of the implant 100 (including both the front height HF and the rear height HR) may be varied based on the intended location of implant 100 in the spine. The implant 100 may also have a width W and a depth D (shown in FIG. 2) that may be selected based on a desired location of the implant 100 in the spine. In some implementations, the width W of the implant 100 may be in a range of about 12 millimeter (mm) to 20 mm while the depth D may be in a range of about 10 mm to 18 mm. For example, depending on the curvature in the spine being treated (e.g., lordosis) and the intended location for the implant 100, the size and dimensions of the implant 100 may be varied. As will be appreciated, these dimensions of the implant 100 are only examples and are not intended to limit the scope of the present disclosure.

Figure 2:
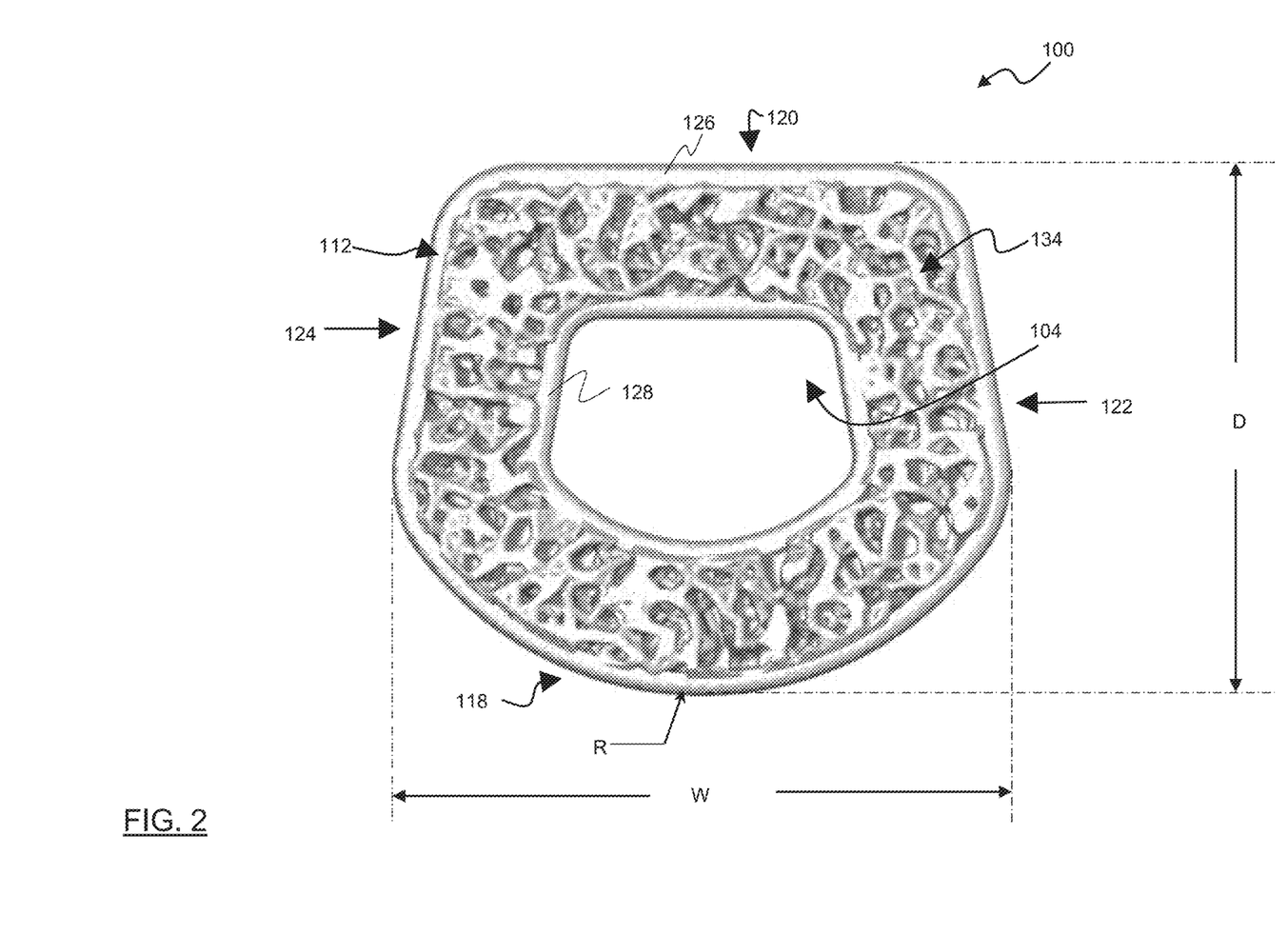
FIG. 2 illustrates a top view of the intervertebral implant, in accordance with an aspect of the present disclosure.

In an embodiment, as shown from the top in FIG. 2, the sides 122, 124 of the implant body 102 may diverge radially outward from the rear portion 120 towards the front portion 118, and the front portion 118 may have an arcuate, e.g., a convex profile, having a radius of curvature R, thereby defining a composite circular-trapezoidal profile (i.e., a combination of trapezoid and circle) for the implant 100. In some examples, the profile of the implant 100, e.g., the composite circular-trapezoidal profile may correspond to a transverse cross-section profile taken along the axial plane and may thus extend along the entire height of the implant 100. In some other examples, the sides 122, 124 may extend parallel to one another between the front portion 118 and the rear portion 120 to define a composite circular-rectangular (e.g., a D-shaped) cross-sectional profile for the implant 100. Further, in some yet other examples, the transverse cross-sectional profile of the implant 100 may have a basic geometric profile, such as, but not limited to, a substantially square, rectangular, or circular profile. Further, in some examples, the central cavity 104 may also have the same transverse cross-sectional profile as that of the implant 100, however, in some other examples, the two may have different profiles. For example, the implant 100 may have a substantially square or rectangular profile whereas the central cavity 104 may have a substantially circular or semi-circular profile.

Figure 3:
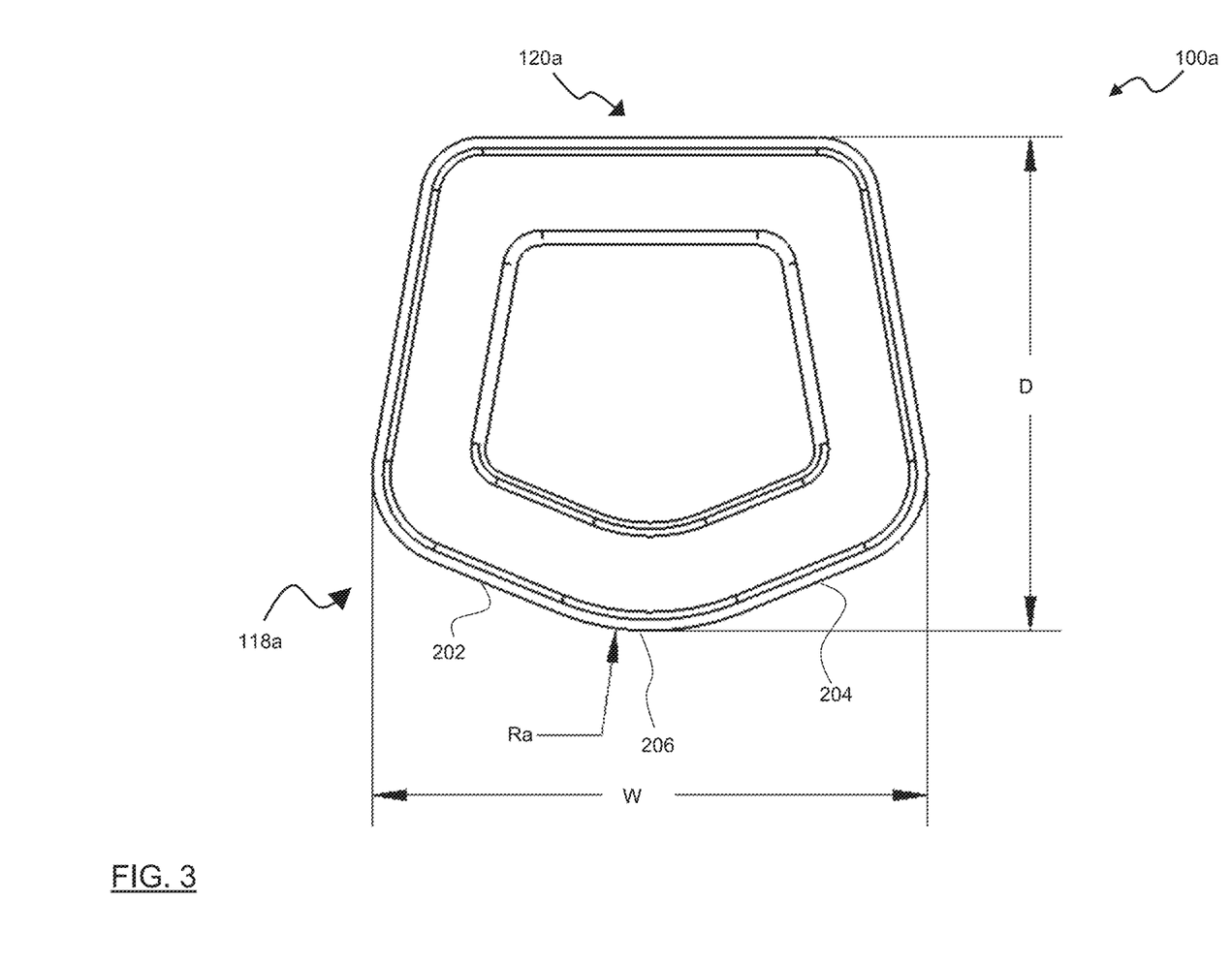
FIG. 3 illustrates a top view of an intervertebral implant, in accordance with another aspect of the present disclosure.

In an alternative implementation, such as that shown in FIG. 3, instead of a simple arcuate front portion, the implant (shown as implant 100a) may have a rounded triangular profile at the front portion 118a, thereby defining a composite rounded triangular-trapezoidal cross-sectional profile for the implant 100a. In such cases, the front portion 118a may include a pair of converging sections 202 and 204 connected at a rounded or arcuate joint 206 that has a radius of curvature Ra. As will be appreciated, the profile of the front portion 118, 118a may be selected based on the size and end application of the implant 100. For example, for larger sizes, the implant with the rounded triangular front portion 118a may be used while for smaller sizes, the implant having arcuate front portion 118 may be used. However, these are merely examples and are not intended to limit the scope of the claimed subject matter in any manner. Moreover, the rounded triangular profile of the front portion 118a also provides an easy connection for an insertion tool to engage with the implant 100a.

Further, referring back to FIGS. 1 and 2, the top plate 112 may define a top outer rim 126 disposed continuously along an outer periphery and a top inner rim 128 extending continuously along an inner periphery of the top plate 112.

The top inner rim 128 is disposed radially inward from the top outer rim 126 and configured to communicate with the central cavity 104. Each of the top outer rim 126 and the top inner rim 128 is configured to extend vertically downward along the longitudinal axis 110 to define a top outer wall 130 disposed on the external surface 106 and a top inner wall 132 disposed on the internal surface 108 of the implant 100.

In an example implementation, the top plate 112 may further include a top engagement surface 134 disposed to continually extend between the top outer wall 130 and the top inner wall 132. The top engagement surface 134 may be configured to engage with a vertebral tissue, such as the tissue of vertebral body above the implant 100, when the implant 100 is positioned in place between the two adjacent vertebral bodies. The top engagement surface 134 may be designed suitably to facilitate proper engagement with the vertebral tissue and also stimulate bone growth to promote osseointegration. Thus, the top engagement surface 134, may, for example, include a rough, textured, porous, semi-porous, dimpled, knurled, toothed, grooved and/or polished surface. In an embodiment, as illustrated, the top engagement surface 134 may include a semi-porous scaffold having pores, such that the scaffold is disposed to protrude longitudinally upward from the top outer rim 126 and the top inner rim 128. It may be appreciated that the size of the pores may be suitably selected so as to allow bony ingrowth yet still provide scaffolding support to compressive and torsional forces.

Further, the bottom plate 114 may also include a bottom outer rim 136 and corresponding bottom outer wall 138, a bottom inner rim and a corresponding bottom inner wall (not shown) surrounding and communicating with the central cavity 104, and a bottom engagement surface 140 implemented in a similar manner as described above for the top plate 112. Further, the bottom engagement surface 140, may also include a semi-porous scaffold disposed between and protruding longitudinally downward from bottom outer rim 136 and the bottom inner rim of the bottom plate 114. In some embodiments, the top plate 112 and the bottom plate 114 may be identical and may be positioned or used interchangeably, thereby making the implant body 102 reversible along the longitudinal axis 110. In some alternative implementations, the top plate 112 and the bottom plate 114 may have different configurations to achieve similar results without deviating from the scope of this disclosure.

Figure 4:
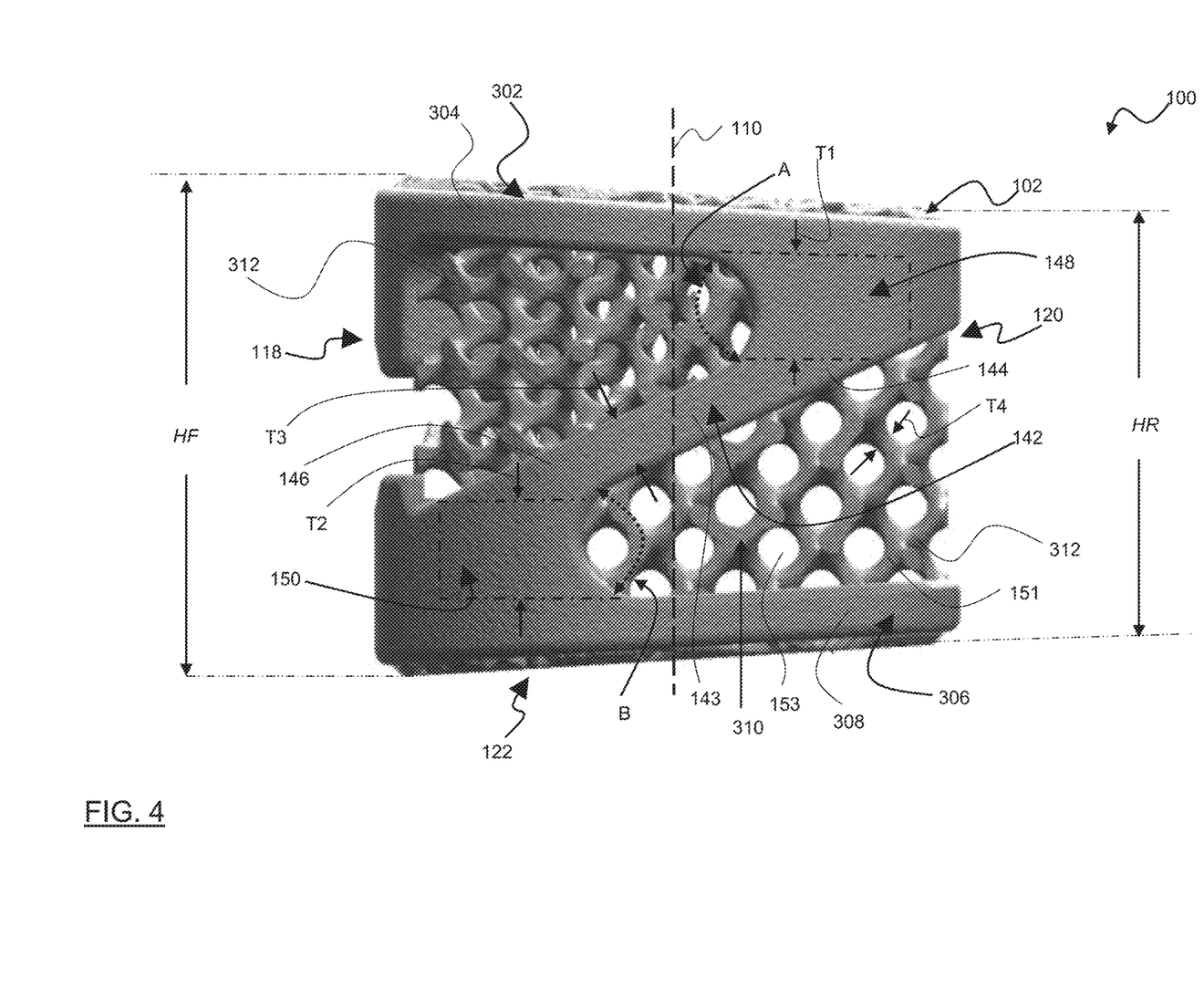
FIG. 4 illustrates a side elevation view of the intervertebral implant, in accordance with an aspect of the present disclosure.

Referring now to FIG. 4, one of the sides 122, 124, e.g., the first side 122 of the implant 100 is illustrated. As shown, the first side 122 of the implant 100 includes a first portion 302 of the top plate 112 (referred to as the first top plate portion 302), a first portion 304 of the top outer wall 130 (referred to as the first top outer wall portion 304), a first portion 306 of the bottom plate 114 (referred to as the first bottom plate portion 306), a first portion 308 of the bottom outer wall 138 (referred to as the first bottom outer wall portion 308) and a first portion 310 of the encircling wall 116 (referred to as the first encircling wall portion 310). In one embodiment of the present disclosure, the first side 122 includes a cross-arm 142 obliquely extending between the first top plate portion 302 and the first bottom plate portion 306. The cross-arm 142 is configured to form a part of the first encircling wall portion 310 and may be disposed at a first angle A with respect to the first top plate portion 302 and a second angle B with respect to the first bottom plate portion 306, thereby forming a "Z" or "S" shaped support structure on the first side 122 of the implant 100. In some examples, the angles A and B may correspond to alternating interior angles and may be equal. The cross-arm 142 may have a first end 144 transitioning to merge with the first top plate portion 302 towards and proximal to the rear portion 120 of the implant 100. The cross-arm 142 may have a second end 146 transitioning to merge with the first bottom plate portion 306 towards and proximal to the front portion 118 of the implant 100. A vice-versa configuration of the cross-arm 142 may also be implemented without deviating from the scope of the present disclosure. Thus, for example, in some alternative embodiments, the first end 144 may be joined to the first top plate portion 302 towards and proximal to the front portion 118 while the second end 146 may be joined to the first bottom plate portion 306 towards and proximal to the rear portion 120 of the implant 100. Further, the second side 124 of the implant 100 may also have a respective cross-arm (not shown) obliquely extending between the respective portions, i.e., second portions (not shown) of the top plate 112 and the bottom plate 114 to define a similar "Z" or "S" shaped support structure thereon. The cross-arm support structure is configured to provide a degree of flexibility to the implant 100 to resiliently withstand and absorb the compressive loads applied thereon, as will be described herein. It may be appreciated that in certain alternative embodiments, two cross-arms instead of one may be positioned in an X-shaped configuration to achieve similar results. In some yet other embodiments, multiple cross-arms may be positioned to form stacked Z-shaped configurations. As further described herein, and as would be appreciated by persons skilled in the art, by varying the shape and thickness of the cross-arms 142, the stiffness of the implant 100 can be increased or decreased.

In some implementations, the cross-arm 142 may extend to cover an entire lateral space (i.e., transverse to the longitudinal axis 110) between the first outer wall portions 304, 308 and the inner walls (not shown) of the first top plate portion 302 and the first bottom plate portion 306, respectively. In such examples, a lateral thickness of the cross-arm 142 may be equal to the distance between the inner wall portions and the corresponding outer wall portions 304, 308 on each of the first top plate portion 302 and the first bottom plate portion 306. In some alternative implementations, the cross-arm 142 may extend to cover only a part of the lateral space between the walls. In such implementations, the lateral thickness of the cross-arm 142 may be less than the distance between the inner and the outer walls. The second side 124 may also include the respective cross-arm implemented in a similar manner. It may be appreciated that varying such lateral thickness of the cross-arm(s) 142 may result in corresponding variation in the stiffness of the implant 100.

The first end 144 of the cross arm 142 may be configured to transition and merge with the first top plate portion 302, thereby defining a top transition section 148 disposed therebetween. The second end 146 may be configured to transition and merge with the first bottom plate portion 306, thereby defining a bottom transition section 150 disposed therebetween. In an embodiment, each of the top transition section 148 and the bottom transition section 150 may have a respective thickness T1, T2, which may be greater than a thickness T3 of a portion 143 of the cross-arm 142 extending between the transition sections 148, 150. In some examples, the thickness T2 of the bottom transition section 150 may be greater than the thickness T1 of the top transition section 148. In some other implementations, the thickness T1 and T2 of the top transition section 148 and the bottom transition section 150, respectively, may be equal. Further, the thickness of the transition sections 148, 150 may be increased or decreased to accordingly increase or decrease the stiffness of the implant 100. For example, when the compressive force is applied on the implant 100, the plates 112, 114 on each side 122, 124 may be configured to flex towards one another about the respective transition sections 148, 150, thereby decreasing the angles A and B between the respective cross-arms 142 and the portions (e.g., first portions 302, 306) of the plates 112, 114. Therefore, the thickness T1, T2 of the transition sections 148, 150 may be configured to control the degree of bending permissible for the plates 112, 114 and accordingly for the implant 100. Thus, by increasing the thickness T1, T2 of one or more of the respective transition sections 148, 150, the degree of bending can be reduced, thereby increasing the stiffness of the implant 100. Similarly, by decreasing the thickness T1, T2 of the transition sections 148, 150, the permissible degree of bending may be increased, thereby increasing the flexibility (and decreasing the stiffness) of the implant 100. Additionally, the cross-arm 142 may also be modified by adjusting their thickness T3, thereby allowing a gradual change in stiffness characteristics to be provided along their length.

Further, in an embodiment of the present disclosure, the implant body 102 may also include a lattice structure 152 disposed on the encircling wall 116. As shown in FIG. 4, the first side 122 includes a first portion 312 of the lattice structure 152 (referred to as the first lattice portion 312) extending between the first top plate portion 302 and the cross arm 142 and between the first bottom plate portion 306 and the cross-arm 142 on the first encircling wall portion 310. Further, a second portion (not shown) of the lattice structure 152 may also be disposed on the second side 124 between the respective top plate portion, the respective cross-arm, and the bottom plate portion therein, in a similar manner. In an embodiment, the lattice structure 152 may be implemented in the form of material foam having scaffold comprising a number of lattice components 151 connected together to define pores 153 disposed in a randomized pattern. In some alternative embodiments, the pores 153 may be disposed in a predefined non-randomized pattern to achieve similar results. It may be appreciated that the size of the pores 153 may be suitably selected so as to allow bony ingrowth yet still provide scaffolding support to compressive and torsional forces. Further, the size of the pores 153 may be varied to adjust the stiffness of the implant 100. For example, a lattice with large pores, such as that illustrated herein, may be less stiff than a dense lattice with small pores. Further, a thickness T4 of the individual lattice components 151 of the lattice structure 152 may also be varied to accordingly vary the stiffness of the implant 100.

Figure 5:
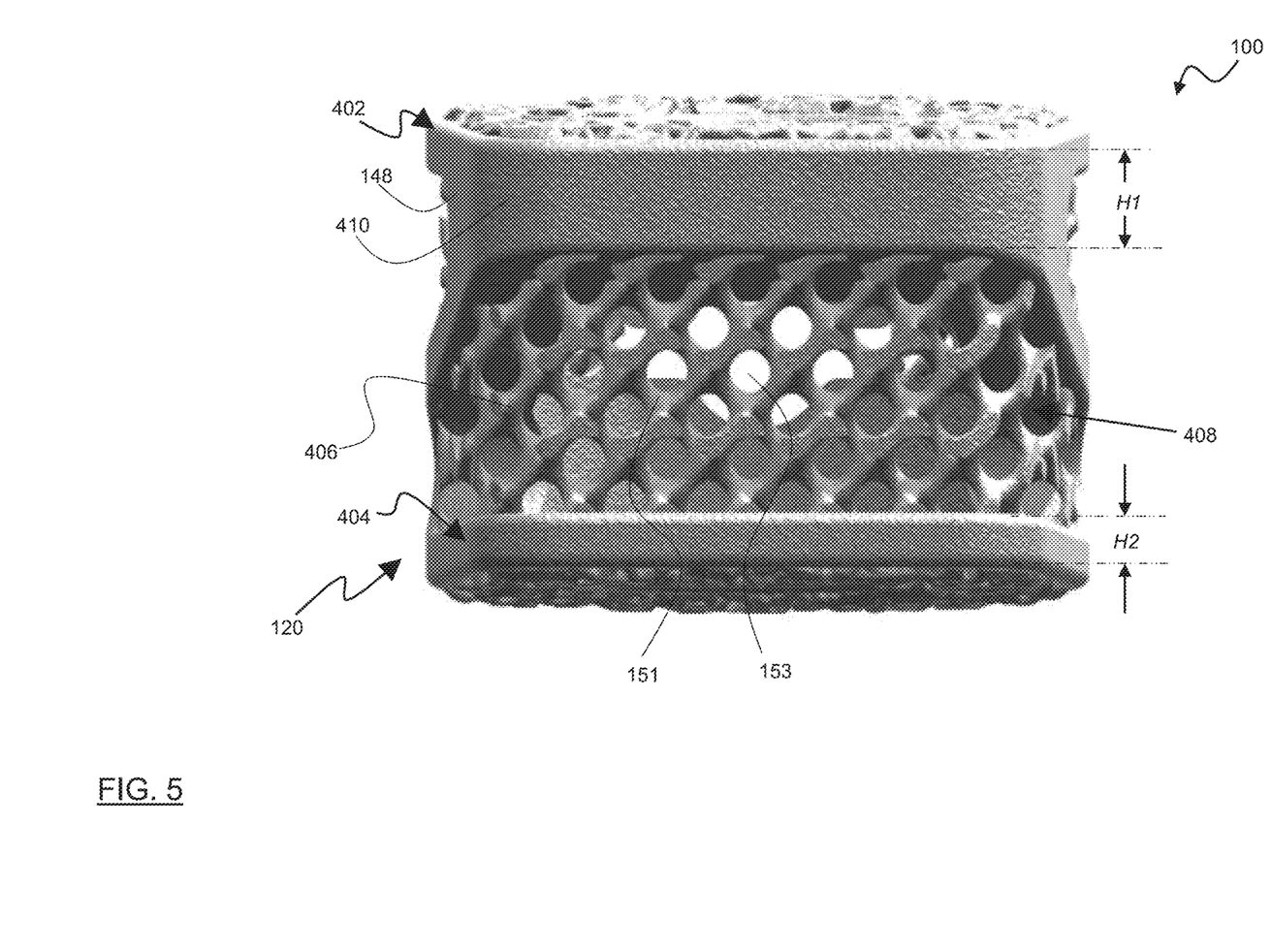
FIG. 5 illustrates a rear elevation view of the intervertebral implant, in accordance with an aspect of the present disclosure.

Referring now to FIG. 5, the rear portion 120 of the implant 100 is illustrated. As shown, the rear portion 120 includes a third portion 402 of the top plate 112 (referred to as the third top plate portion 402), a third portion 404 of the bottom plate 114 (referred to as the third bottom plate portion 404). In an embodiment, the rear portion 120 may further include a third portion 406 of the lattice structure 152 (referred to as the third lattice portion 406) extending continually between the third top plate portion 402 and the third bottom plate portion 404. Thus, in the illustrated embodiment, a third portion 408 of the encircling wall 116 (referred to as the third encircling wall portion 408) in the rear portion 120 of the implant 100 is substantially open including only the third lattice portion 406 extending across the lateral width of the wall portion 408. It may be appreciated that one or more characteristics of the third lattice portion 406 in the rear portion 120, e.g., thickness of the lattice components 151 and the pores 153, density, material, etc., may be adjusted to provide the desired overall stiffness of the implant 100 in a similar manner as described above for first lattice portion 312 and the second lattice portion. Further, in some examples, such as the one illustrated, the third lattice portion 406 may be configured to continually extend to the sides 122, 124 to merge with the first lattice portion 312 and the second lattice portion positioned, for example, between the cross arm 142 and the respective first bottom plate portion 306 and the second bottom plate portion therein.

In the illustrated embodiment, the third top plate portion 402 in the rear portion 120 may have a height H1 that may be greater than, for example, a height H2 of the third bottom plate portion 404 therein. To this end, in some examples, one or both of a third top outer wall portion 410 of the top outer wall 130 and a third top inner wall portion of the top inner wall (not shown) may extend longitudinally downward to form the height H1 of the third top plate portion 402. Further, in some examples, such as that illustrated, the third top plate portion 402 in the rear portion 120 having the height H1 may also extend to the sides 122, 124 to merge with the respective top transition sections 148 on each side.

Figure 6:
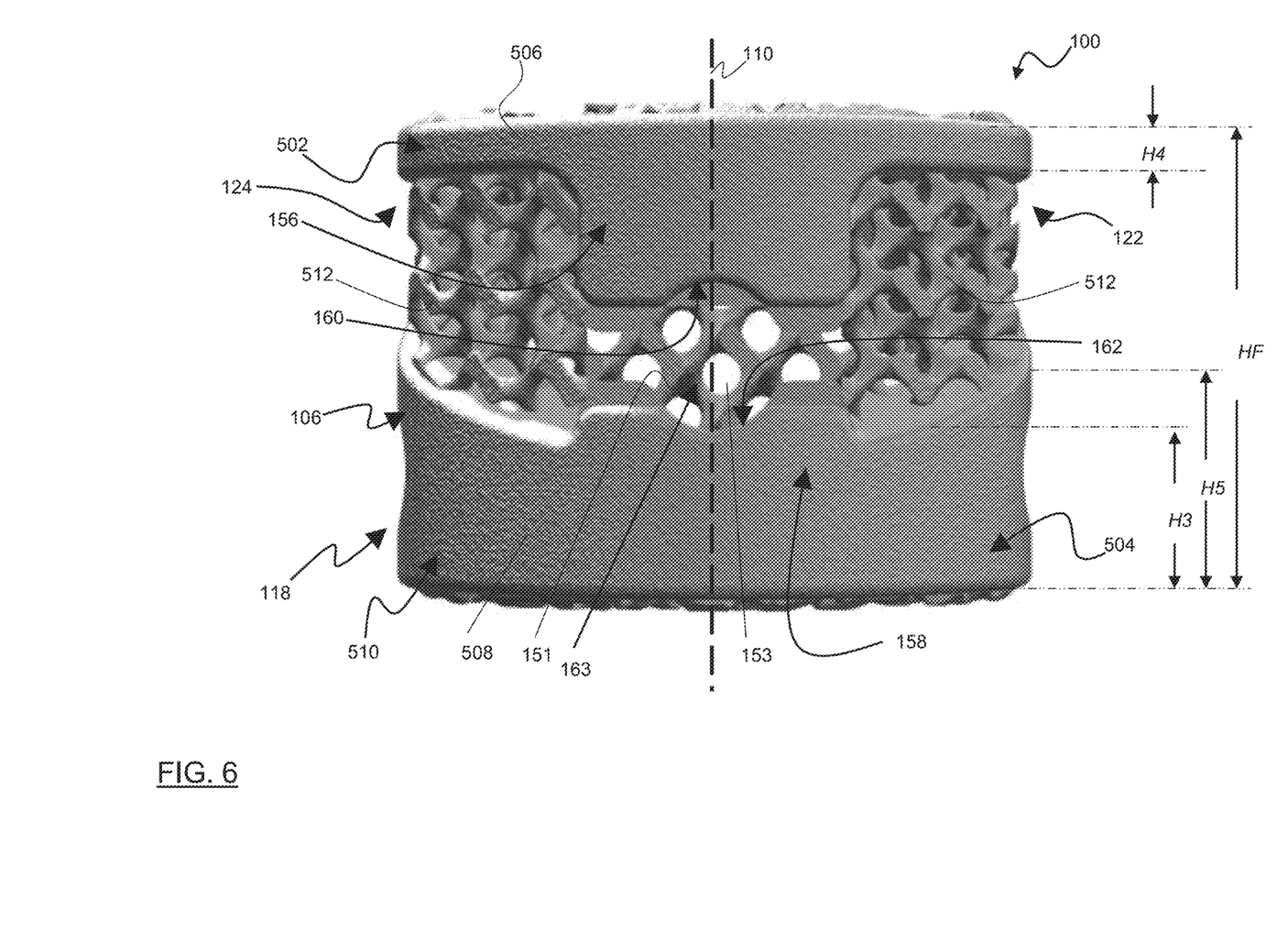
FIG. 6 illustrates a front elevation view of the intervertebral implant, in accordance with an aspect of the present disclosure.

FIG. 6 illustrates the front portion 118 of the implant 100, in accordance with an embodiment of the present disclosure. As illustrated, the front portion 118 includes a fourth portion 502 of the top plate 112 (referred to as the fourth top plate portion 502) and a fourth portion 504 of the bottom plate 114 (referred to as the fourth bottom plate portion 504). In an embodiment, as illustrated, the fourth top plate portion 502 may include a first lip projection 156 extending longitudinally downward from, for example, a fourth top outer wall portion 506 towards the fourth bottom plate portion 504 on the external surface 106 of the implant 100. Similarly, the fourth bottom plate portion 504 may include a second lip projection 158 extending longitudinally upward from, for example, a fourth bottom outer wall portion 508 towards the fourth top plate portion 502 on the external surface 106 of the implant 100. In an example implementation, each of the first lip projection 156 and the second lip projection 158 may extend, for example, longitudinally towards a center of the front portion 118 partially through the front height HF of the implant 100 and be spaced apart from one another. However, in some alternative examples, the first and second lip projections 156, 158 may be positioned elsewhere in the front portion 118, such as proximal to one of the sides 122, 124 instead of being in the center as shown. In some other alternative examples, more than one lip projections or a single wider lip projection may also be provided on one or both of the fourth top plate portion 502 and the fourth bottom plate portion 504.

In an embodiment of the present disclosure, each of the first lip projection 156 and the second lip projection 158 may further define a first notch 160 and a second notch 162, respectively, recessed therein. The lip projections 156, 158 and the notches 160, 162 may extend to form a portion (i.e., fourth portion 510) of the encircling wall 116 in the front portion 118 of the implant 100. The lip projections 156, 158 as well as the notches 160, 162 may be configured to extend radially through the external surface 106 and the internal surface 108 so as to communicate with the central cavity 104. As illustrated, the notches 160, 162 may include complimentary profiles, e.g., concave profiles, and may be spaced apart and aligned longitudinally to define an insert tool recess 163 therebetween. The insert tool recess 163 may be configured to facilitate insertion and engagement of an inserting tool (not shown) for placing the implant 100 in between the vertebral bodies. It may be appreciated that the shape, profile, and position of these notches 160, 162 are merely examples and that they may have any other suitable configurations or positions to achieve similar functionalities.

Further, in an embodiment, as shown, the fourth bottom plate portion 504 may have a height H3 that may be greater than, for example, the height H4 of the fourth top plate portion 502 in the front portion 118. In some examples, the height H3 of the fourth bottom plate portion 504 in the front portion 118 may be equal to or greater than the height H1 of the third top plate portion 402 in the rear portion 120. To this end, for example, one or both of the fourth bottom outer wall portion 508 and a fourth bottom inner wall portion (not shown) in the front portion 118 may extend longitudinally upwards to form the height H3 of the fourth bottom plate portion 504. Further, in some examples, such as that illustrated, the height H3 of the fourth bottom plate portion 504 is configured to incrementally transition to height H5 as the fourth bottom plate portion 504 extends and transitions to the sides 122, 124 to merge with the bottom transition sections 150 on each side 122, 124. Thus, the height H5 of the fourth bottom plate portion 504 towards the sides 122, 124 is greater than the height H3 of the same near the lip projection 158 in the front portion 118.

Further, the front portion 118 may also include a fourth portion 512 of the lattice structure 152 (referred to as the fourth lattice portion 512) extending between the fourth top plate portion 502 and the fourth bottom plate portion 504 and adjacent to the lip projections 156, 158. However, as illustrated, the fourth lattice portion 512 may not extend in between the notches 160, 162 to allow for the insertion tool to insert and engage with the central cavity 104 for placing the implant 100 in position. It may be appreciated that one or more characteristics of the fourth lattice portion 512 e.g., thickness of the lattice components 151 and the pores 153, density, material, etc., may be adjusted to adjust the overall stiffness of the implant 100 in a similar manner as described above for first, second and the third lattice portions. Further, in some examples, such as the one illustrated, the fourth lattice portion 512 may be configured to continually extend to the sides 122, 124 to merge with the respective portions of the lattice 152 positioned, for example, between the cross arm 142 and the respective portions of the top plate 112 therein.

Figure 7:
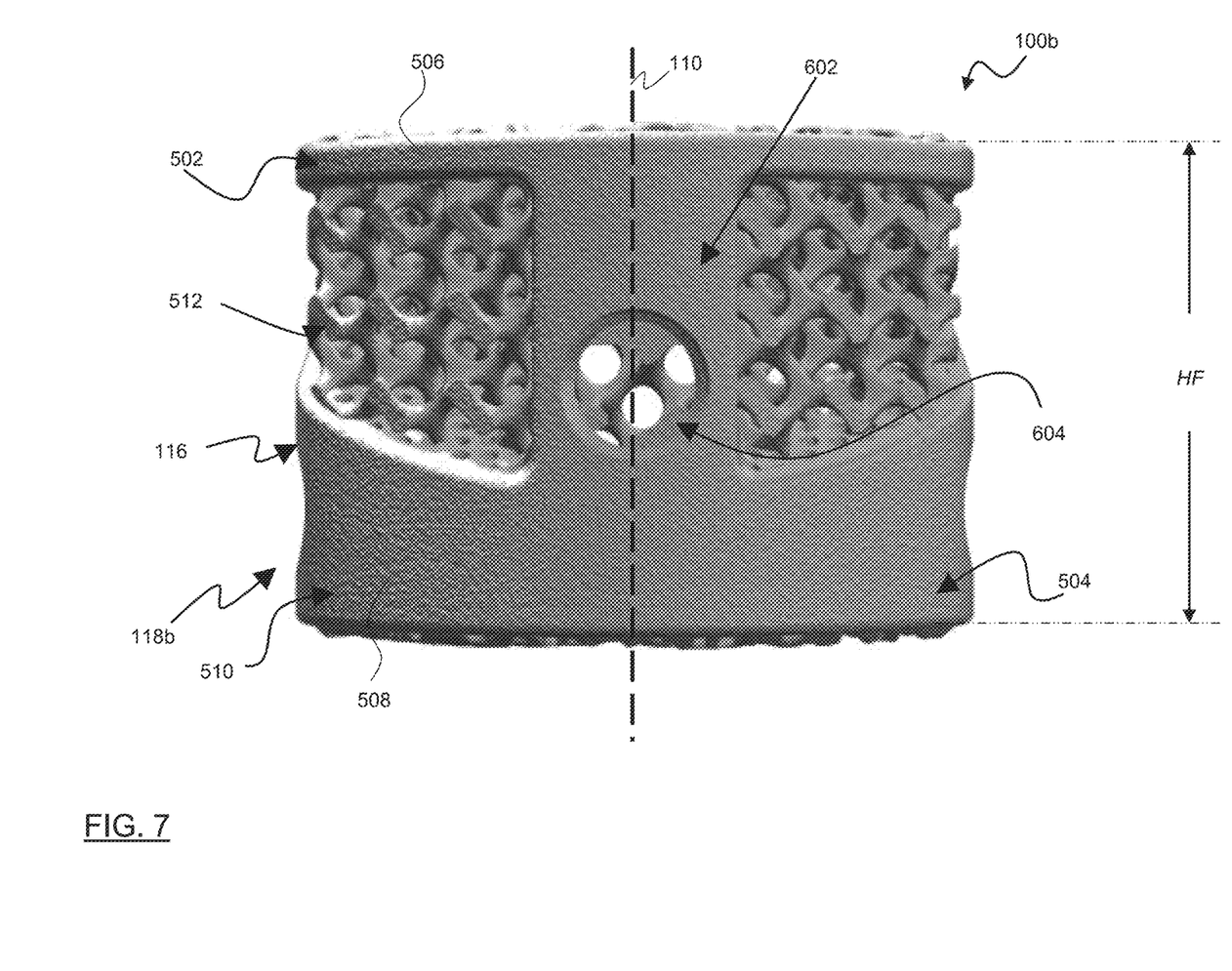
FIG. 7 illustrates a front elevation view of an intervertebral implant, in accordance with another aspect of the present disclosure.

Referring now to FIG. 7, an alternative structural implementation of the front portion, hereinafter referred to as the front portion 118b of the implant, hereinafter referred to as the implant 100b is illustrated. In this embodiment, as illustrated, the lip projections and the notches may be formed as a single component, hereinafter referred to as the lip projection 602, to define an insert slot 604 configured to receive and engage with the inserting tool. The insert slot 604 may be configured to extend through the fourth portion 510 of the encircling wall 116 in the front portion 118b between the external surface and the internal surface so as to communicate with the central cavity. In an embodiment, the insert slot 604 may have a circular profile and may include a threaded receptacle (not shown) for engaging with the insert tool. The position and configuration of the insert slot 604 are only examples and it may be contemplated that any other suitable configurations may also be implemented to achieve similar functionalities without deviating from the scope of the present disclosure.

It may be appreciated that the various components of the implant 100, 100a, 100b such as the plates 112, 114 (including their respective portions on the front, rear and the sides), the cross-arm(s) 142, the lattice structure 152, the lip projections 156, 158, 602, the notches 160, 162 and the insert slots 163, 604 are described separately solely for the ease of explanation and that they may be manufactured as a single integrated component and/or separate components combined together, without deviating from the scope of the present disclosure. Further, the implant 100, 100a, 100b, may be formed by using a 3D printing process, such as selective laser sintering (SLS), selective laser melting (SLM), or electron beam melting (EBM). However, it may be contemplated that depending on the final design of the implant 100, 100a, 100b, other manufacturing processes may also be used instead.

In various implementations of the present disclosure, one or more components of implants 100, 100a, 100b may be manufactured from the same or different materials. In an embodiment, the implants 100, 100a, 100b, may be made of titanium or titanium alloys, such as grade 23 titanium as per American Society for Testing and Materials (ASTM) F3001 standards. However, in some other implementations, the implants 100, 100a, 100b, may also be made from other known materials known in the art, for example, carbon fiber, simple or advanced plastics such as polyether-etherketone (PEEK), shape metal alloys such as Nitinol™ or more commonly used materials such as cobalt chrome, or stainless steel.

The implants 100, 100a, 100b, according to the various embodiments described herein provide physiological stiffness to the spinal segment where they are implanted while still permitting a range of motion for the adjacent vertebrae. For example, when the compressive force is applied on the implant(s) 100, 100a, 100b, free or distal ends of the plates 112, 114 (i.e., the ends of the plates 112, 114 radially opposite to the transition sections 148, 150) may longitudinally flex towards one another and about the transition sections 148, 150 of the cross-arm 142 on each of the first and the second sides 122, 124, thereby decreasing the angles A and B between the cross-arm 142 and the plates 112, 114. This bending is restricted or controlled by the lattice structure 152, which resists the compressive forces acting on the implant 100, 100a, while providing a certain degree of resilience along the longitudinal axis 110 against the acting loads (such as due to the pore size, elasticity, and tensile strength of the material, and/or thickness T4 of the lattice components in the lattice structure 152). This way, the Z-shaped support structure (including the plates 112, 114, the cross-arm 142 and the transition sections 148, 150) and the lattice structure 152 facilitates effective absorption of the compressive forces and allow the implant 100, 100a, 100b, to provide the required distraction for the adjacent vertebrae while also retaining the height of the implant 100, 100a, 100b, e.g., when they are positioned in the spine. Thus, the implants 100, 100a, 100b, allow the function of a normal disc to be mechanically mimicked, thereby restoring motion segment stiffness.

Further, the implants 100, 100a, 100b, according to the various embodiments of the present disclosure, possess a stiffness that facilitates withstanding the physiologic loading in the spine while avoiding significant subsidence into the adjacent vertebral bodies. In an embodiment of the present disclosure, the implant 100, 100a, 100b, possesses a stiffness within a predefined range, such as, from 13,000 Newton per millimeter (N/mm) to 25,000 N/mm. For example, the predefined range for stiffness may be equivalent to a range defined by a health regulatory body, such as the FDA, and may correspond to an acceptable range of stiffness for an implant when it is tested against various loads, such as static axial compression, static compression-shear, dynamic axial compression loads, and so on. As explained above, one or more components of the implant(s) 100, 100a, such as the cross arm 142, the transition sections 148, 150, the lattice structures 152, the lip projections 156, 158, 602 and so on, may contribute to the overall stiffness of the implant 100, 100a, 100b, and thus, varying one or more characteristics of these components may accordingly impact the stiffness of the implants 100, 100a, 100b. For example, the size of the pores 153 defined by the lattice structure 152, thickness of the lattice components 151 in the lattice structure 152, thickness of the transition sections 148, 150, thickness of the cross-arm 142, the dimensions of the lip projections 156, 158, material of one or more components of the implant 100, 100a, 100b, and so on, may be varied to gradually vary the stiffness of the implant 100, 100a, 100b, for example, to achieve a stiffness within a different predefined range of values that may be provided by the regulatory bodies.

Furthermore, the lattice structure 152 also promotes bone growth therethrough to facilitate efficient osseointegration of the implants 100, 100a, 100b, in the spine. For example, the exposed lattice structure 152 may directly contact vertebrae or other bone that is desired to anchor into the implant 100, 100a, 100b, thereby healing the bone graft together through and alongside the implants 100, 100a, 100b. In some implementations, bone growth may be further facilitated through use of a coating on the lattice structure 152 and/or other features of the implants 100, 100a, 100b. For example, the lattice structure 152 may be provided with an osteo-integration coating or may be roughened to provide additional surface area that contacts bone graft material.

In use, an insert tool (not shown) is inserted into the aligned notches 160,164 and/or the insert slot 604 and the implants 100, 100a, 100b, are then inserted into the designated disc space between the adjacent vertebral bodies of the spine, so as to engage the top engagement surface 134 and the bottom engagement surface 140 with the tissues of the respective adjacent vertebral bodies. However, in some other examples, the implant(s) 100, 100a, 100b, of the present disclosure may also include or be used with one or more artificial endplates or other prosthetic devices. Once positioned within the disc space, the implants 100, 100a, 100b, are allowed to bear against the respective adjacent vertebral bodies within the disc space. Continuous and dynamic Y-axis (or vertical) distraction of the spinal segment is generated by implant 100, 100a, 100b, due to the elastic force generated by the Z-shaped support structure and the lattice structure 152, which biases the plates 112, 114, thereby applying a separating force against the adjacent vertebrae.

Although the above description includes reference to certain specific embodiments, various modifications thereof will be apparent to those skilled in the art. Any examples provided herein are included solely for the purpose of illustration and are not intended to be limiting in any way. Any drawings provided herein are solely for the purpose of illustrating various aspects of the description and are not intended to be drawn to scale or to be limiting in any way. The scope of the claims appended hereto should not be limited by the preferred embodiments set forth in the above description but should be given the broadest interpretation consistent with the present specification as a whole. The disclosures of all prior art recited herein are incorporated herein by reference in their entirety.

What is claimed is:

1. An intervertebral implant comprising:
   an implant body having a longitudinal axis, first and second ends and opposed first and second sides, the first and second sides extending between the first and second ends, the body further including:
   a top plate and a bottom plate, wherein the bottom plate is disposed longitudinally opposite and spaced apart from the top plate along the longitudinal axis;
   a first cross-arm provided on the first side of the body, the first arm obliquely extending between the top plate and the bottom plate and from the first end to the second end of the implant body, wherein a first end of the first arm is connected to the top plate proximal to or at the first end of the top plate and a second end of the first arm is connected to the bottom plate proximal to or at the second end of the bottom plate, whereby the top plate, bottom plate, and first arm define a generally "Z" shape;
   a second cross-arm provided on the second side of the body, the second arm obliquely extending between the top plate and the bottom plate and from the first end to the second end of the implant body, wherein a first end of the second arm is connected to the top plate proximal to or at the first end of the top plate and a second end of the second arm is connected to the bottom plate proximal to or at the second end of the bottom plate, whereby the top plate, bottom plate, and second arm define a generally "Z" shape;
   the first cross-arm and second-arm being the only cross arms provided on the first and second sides of the body; and
   the first and second sides including a lattice structure disposed at least between the cross-arms and the top and bottom plates.

2. The intervertebral implant of claim 1, wherein the implant body comprises a structure adapted to define and surround a central cavity and includes an encircling wall extending between the top plate and the bottom plate and surrounding the central cavity, and wherein the encircling wall includes the at least one first cross-arm, the at least one second cross-arm, and the lattice structure.

3. The intervertebral implant of claim 1, wherein the implant body comprises a structure having a transverse cross-section profile being one of a circular-trapezoidal profile, a rounded triangular-trapezoidal profile, a circular-rectangular profile, a circular profile, or a rectangular profile.

4. The intervertebral implant of claim 1, wherein each of the top plate and the bottom plate includes:
   an outer rim;
   an inner rim disposed and spaced radially inward from the outer rim; and
   an engagement surface extending between the outer rim and the inner rim adapted to engage with tissue of vertebral bodies adjacent to the intervertebral implant after implantation.

5. The intervertebral implant of claim 4, wherein the engagement surface comprises a scaffold having a plurality of pores disposed in one of a randomized or a non-randomized pattern and is adapted to protrude outward along the longitudinal axis from the outer rim and the inner rim of the respective one of the top plate and the bottom plate.

6. The intervertebral implant of claim 1, wherein the first end of at least one first cross-arm and at least one second cross-arms comprises a first transition section adjacent the top plate and the second end of at least one first and at least one second cross-arms comprises a second transition section adjacent the bottom plate, and wherein the first transition section and the second transition section comprise thickened regions of the cross-arms.

7. The intervertebral implant of claim 1, wherein the lattice structure includes a plurality of lattice components connected together to form pores disposed in one or more of a randomized or non-randomized pattern.

8. The intervertebral implant of claim 1, wherein the second end of the implant comprises:
 a portion of the top plate and a portion of the bottom plate, the portion of the top plate having a longitudinal height greater than a longitudinal height of the portion of the bottom plate; and
 a lattice portion of the lattice structure extending between the portion of the top plate and the portion of the bottom plate.

9. The intervertebral implant of claim 1, wherein the first end of the implant comprises:
 a portion of the top plate and a portion of the bottom plate, the portion of the top plate including a first lip projection extending longitudinally towards the portion of the bottom plate and the portion of bottom plate including a second lip projection extending longitudinally towards the portion of top plate.

10. The intervertebral implant of claim 9, wherein the first lip projection and the second lip projection define a first notch and a second notch, respectively, and wherein the first notch and the second notch are longitudinally aligned and spaced apart to define an insert tool recess adapted to facilitate insertion and engagement of an inserting tool to place the intervertebral implant in between adjacent vertebral bodies.

11. The intervertebral implant of claim 9, wherein the first lip projection and the second lip projection are joined to define an insert slot configured to facilitate insertion and engagement of an inserting tool to place the intervertebral implant in between adjacent vertebral bodies.

12. The intervertebral implant of claim 9, wherein the first end of the bottom plate has a longitudinal height greater than a longitudinal height of the first end of the top plate.

13. The intervertebral implant of claim 9, wherein the first end of the implant body includes a lattice portion of the lattice structure extending between the portion of the top plate and the portion of the bottom plate and surrounding each of the first lip projection and the second lip projection.

14. The intervertebral implant of claim 1, wherein the first end and the second end of the implant each has a height in the direction of the longitudinal axis, and wherein the height of the first end is greater than the height of the second end.

15. The intervertebral implant of claim 14, wherein the first and second sides of the implant diverge radially outwardly from the second end towards the first end, and wherein the first end comprises an arcuate profile to define a circular trapezoidal profile of the intervertebral implant.

16. The intervertebral implant of claim 1, wherein the top plate has a height at the second end greater than a height at the first end and the bottom plate has a height at the first end greater than a height at the second end.

17. The intervertebral implant of claim 1, wherein the implant body, the bottom plate, the top plate, the cross-arms, and the lattice structure are independently made of one or more of titanium or titanium alloys, carbon fiber, polyetheretherketone (PEEK), or shape metal alloys.

18. The intervertebral implant of claim 1, wherein the at least one first arm and the at least one second arm extend in a generally parallel direction.

19. The intervertebral implant of claim 1, wherein the first end of the implant comprises the anterior end and the second end of the implant comprises the posterior end when the implant is in use.

20. The intervertebral implant of claim 1, wherein the first end of the implant comprises the posterior end and the second end of the implant comprises the anterior end when the implant is in use.

* * * * *